United States Patent
Fessler et al.

(10) Patent No.: US 8,233,682 B2
(45) Date of Patent: Jul. 31, 2012

(54) METHODS AND SYSTEMS FOR IMPROVING SPATIAL AND TEMPORAL RESOLUTION OF COMPUTED IMAGES OF MOVING OBJECTS

(75) Inventors: Jeffrey Allen Fessler, Ann Arbor, MI (US); Charles Addison Bouman, West Lafayette, IN (US); Jiang Hsieh, Brookfield, WI (US); Jean-Baptiste Daniel Marie Thibault, Milwaukee, WI (US); Ken David Sauer, South Bend, IN (US); Samit Kumar Basu, Niskayuna, NY (US); Bruno Kristiaan Bernard De Man, Clifton Park, NY (US)

(73) Assignees: General Electric Company, Schenectady, NY (US); The University of Notre Dame du Lac, Notre Dame, IN (US); The Regents of the University of Michigan, Ann Arbor, MI (US); Purdue Research Foundation, West Lafayette, IN (US)

( * ) Notice: Subject to any disclaimer, the term of this patent is extended or adjusted under 35 U.S.C. 154(b) by 986 days.

(21) Appl. No.: 11/758,166

(22) Filed: Jun. 5, 2007

(65) Prior Publication Data

US 2008/0304726 A1 Dec. 11, 2008

(51) Int. Cl.
*G06K 9/00* (2006.01)

(52) U.S. Cl. ........ 382/128; 382/129; 382/130; 382/131; 378/49; 378/82

(58) Field of Classification Search .......... 382/128–131; 378/49, 82
See application file for complete search history.

(56) References Cited

U.S. PATENT DOCUMENTS

| | | | | |
|---|---|---|---|---|
| 5,442,672 | A * | 8/1995 | Bjorkholm et al. | 378/4 |
| 6,103,350 | A * | 8/2000 | Grangeat et al. | 428/195.1 |
| 6,507,633 | B1 | 1/2003 | Elbakri et al. | |
| 6,754,298 | B2 | 6/2004 | Fessler | |
| 6,768,782 | B1 | 7/2004 | Hsieh et al. | |
| 6,850,585 | B2 | 2/2005 | Hsieh et al. | |
| 6,907,102 | B1 * | 6/2005 | Sauer et al. | 378/19 |
| 7,103,204 | B1 * | 9/2006 | Celler et al. | 382/131 |
| 7,221,728 | B2 | 5/2007 | Edic et al. | |
| 7,583,780 | B2 * | 9/2009 | Hsieh et al. | 378/4 |
| 7,783,092 | B2 * | 8/2010 | Agam et al. | 382/128 |
| 2006/0104408 | A1 * | 5/2006 | Thibault et al. | 378/4 |
| 2006/0215891 | A1 * | 9/2006 | Fessler et al. | 382/128 |
| 2007/0116381 | A1 | 5/2007 | Khamene | |
| 2007/0297660 | A1 * | 12/2007 | Hsieh et al. | 382/131 |

OTHER PUBLICATIONS

Mixture—FMRI data, Woolrich et al., 0278-0062, IEEE, 2005, pp. 1-11.*
3D representation—images, Clarysse et al., 0276-6547, IEEE, 19194, pp. 657-660.*

(Continued)

*Primary Examiner* — Jayesh A Patel
(74) *Attorney, Agent, or Firm* — Armstrong Teasdale LLP

(57) ABSTRACT

A method of improving a resolution of an image using image reconstruction is provided. The method includes acquiring scan data of an object and forward projecting a current image estimate of the scan data to generate calculated projection data. The method also includes applying a data-fit term and a regularization term to the scan data and the calculated projection data and modifying at least one of the data fit term and the regularization term to accommodate spatio-temporal information to form a reconstructed image from the scan data and the calculated projection data.

20 Claims, 3 Drawing Sheets

OTHER PUBLICATIONS

Spatial Regularization—mapping, Velipasaoglu et al., 0018-9294, IEEE, 2000, pp. 327-337.*

Estimating—Registration., Zeng et al., 0278-0062., IEEE, 2007, pp. 153-163.*

4D deformable—segmentation., Montagnat et al., 1361-8415, Elsevier, pp. 87-100.*

S.G. Kohlmyer, D. Mattes, H. Vesselle, and T.K. Lewellen, "Application of CT attenuation maps in PET with respiratory motion correction using gate segmented registration (GSR)". Journal of Nuclear Medicine (Abs. book), 2001. (1 page).

R.R. Fulton, B.F. Hutton, M. Braun, B. Ardekani, and R. Larkin, "Use of 3D reconstruction to correct for patient motion in SPECT". Phys. Med. Biol., 39(3), pp. 563-574, Mar. 1994. (12 pgs).

M. Menke, M.S. Atkins, and K.R. Buckley, "Compensation Methods for Head Motion Detected During PET Imaging". IEEE Transactions on Nuclear Science, vol. 43, No. 1, Feb. 1996, pp. 310-317. (8 pgs).

S.R. Goldstein, M.E. Daube-Witherspoon, M.V. Green, and A. Eidsath, "A Head Motion Measurement System Suitable for Emission Computed Tomography". IEEE Transactions on Medical Imaging, vol. 16, No. 1, Feb. 1997, pp. 17-27. (11 pgs).

Y. Picard and C.J. Thompson, "Motion Correction of PET Images Using Multiple Acquisition Frames". IEEE Transactions on Medical Imaging, vol. 16, No. 2, Apr. 1997, pp. 137-144 (8 pgs).

R.R. Fulton, S. Eberl, S.R. Meikle, B.F. Hutton, and M. Braun, "A Practical 3D Tomogrphic Method for Correcting Patient Head Motion in Clinical SPECT", IEEE Transactions on Nuclear Science, vol. 46, No. 3, Jun. 1999, pp. 667-672 (6 pgs).

R.R. Fulton, S.R. Meikle, S. Eberl, J. Pfeiffer, C.J. Constable, and M.J. Fulham, "Correction for Head Movements in Positron Emission Tomography Using an Optical Motion-Tracking System", IEEE Transactions on Nuclear Science, vol. 49, No. 1, Feb. 2002, pp. 116-123 (8 pgs).

C.R. Crawford, K.F. King, C.J. Ritchie, and J.D. Godwin, "Respiratory Compensation in Projection Imaging Using a Magnification and Displacement Model", IEEE Transactions on Medical Imaging, vol. 15, No. 3, Jun. 1996, pp. 327-332 (6 pgs).

C.J. Ritchie, C.R. Crawford, J.D. Godwin, K.F. King, and Y. Kim, "Correction of Computed Tomography Motion Artifacts Using Pixel-Specific Back-Projection", IEEE Transactions on Medical Imaging, vol. 15, No. 3, Jun. 1996, pp. 333-342 (10 pgs).

S. Roux, L. Desbat, A. Koenig, and P. Grangeat, "Exact reconstruction in 2D dynamic CT: compensation of time-dependent affine deformations", Phys. Med. Biol. 49(11), Jun. 2004, pp. 2169-2182 (14 pgs).

B. Thorndyke, E. Schreibmann, P. Maxim, B. Loo, A. Boyer, A. Koong, and L. Xing, "Enhancing 4D PET Through Retrospective Stacking", Proc. Amer. Assoc. Phys. Med., 32(6), Jun. 2005, p. 2096 (1 page).

C.J. Ritchie, J. Hsieh, M.F. Gard, J.D. Godwin, Y. Kim, and C.R. Crawford, "Predictive Respiratory Gating: A New Method to Reduce Motion Artifacts on CT Scans", Radiology, 190(3), Mar. 1994, pp. 847-852 (6 pgs).

S.A. Nehmeh, Y.E. Erdi, C.C. Ling, K.E. Rosenzweig, H. Schoder, S.M. Larson, H.A. Macapinlac, O.D. Squire, and J.L. Humm, "Effect of Respiratory Gating on Quantifying PET Images of Lung Cancer", The Journal of Nuclear Medicine, vol. 43, No. 7, Jul. 2002, pp. 876-881 (6 pgs).

S.S. Vedam, P.J. Keall, V.R. Kini, H. Mostafavi, H.P. Shukla, and R. Mohan, "Acquiring a four-dimensional computed tomography dataset using an external respiratory signal", Phys. Med. Biol. 48(1), Jan. 2003, pp. 45-62 (18 pgs).

Y. Chen, H. Kudo, F. Noo, and M. Defrise, "Accurate and Efficient Image Reconstruction for Spatio-Temporal CT", In Proc. IEEE Nuc. Sci. Symp. Med. Im. Conf., vol. 6, 2004, pp. 3987-3991.

B. De Man, P.M. Edic, and S. Basu, "An iterative algorithm for time-resolved reconstruction of a CT scan of a beating heart", In Proc. Intl. Mtg. on Fully 3D Image Recon. in Rad. and Nuc. Med., 2005, pp. 356-359 (4 pgs).

R.A. Jones, O. Haraldseth, T.B. Muller, P.A. Rinck and A.N. Oksendal, "K-Space Substitution: A Novel Dynamic Imaging Technique", Mag. Res. Med., 29, 1993, pp. 830-834 (5 pgs).

J.J. van Vaals, M.E. Brummer, W.T. Dixon, H.H. Tuithof, H. Engels, R.C. Nelson, B.M. Gerety, J.L. Chezmar, and J.A. den Boer, ""Keyhole" Method for Accelerating Imaging of Contrast Agent Uptake", Mag. Res. Med., vol. 3, No. 4, Jul./Aug. 1993, pp. 671-675 (5 pgs).

U. Schmitt, A.K. Louis, F. Darvas, H. Buchner, and M. Fuchs, "Numerical Aspects of Spatio-Temporal Current Density Reconstruction from EEG-/MEG-Data", IEEE Transactions on Medical Imaging, vol. 20, No. 4, Apr. 2001, pp. 314-324 (11 pgs).

S. Lee, D. Noll and J. Fessler, EXTended Rosette ACquisition Technique (ESTRACT): a dynamic R2 mapping method using extended rosette trajectory, Proc. Intl. Soc. Mag. Reson. Med., 11, 2004, p. 2128 (1 page).

D.R. Gilland, B.A. Mair, J.E. Bowsher, and R.J. Jaszczak, "Simultaneous Reconstruction and Motion Estimation for Gated Cardiac ECT", IEEE Transactions on Nuclear Science, vol. 49, No. 5, Oct. 2002, pp. 2344-2349 (6 pgs).

Z. Cao, D.R. Gilland, B.A. Mair, and R.J. Jaszczak, "Three-Dimensional Motion Estimation With Image Reconstruction for Gated Cardiac ECT", IEEE Transactions on Nuclear Science, vol. 50, No. 3, Jun. 2003, pp. 384-388 (5 pgs).

P. Grangeat, A. Koenig, T. Rodet, and S. Bonnet, "Theoretical framework for a dynamic cone-beam reconstruction algorithm based on a dynamic particle model", Phys. Med. Biol., 47(15), Aug. 2002, pp. 2611-2625 (15 pgs).

B.F. Hutton, A.Z. Kyme, Y.H. Lau, D.W. Skerrett, and R.R. Fulton, "A Hybrid 3-D Reconstruction/Registration Algorithm for Correction of Head Motion in Emission Tomography", IEEE Transactions on Nuclear Science, vol. 49, No. 1, Feb. 2002, pp. 188-194 (7 pgs).

F. Lamare, T. Cresson, J. Savean, C. Cheze-Le Rest, A. Turzo, Y. Bizais, A.J. Reader, and D. Visvikis, "Affine Transformation of List Mode Data for Respiratory Motion Correction in PET", In Proc. IEEE Nuc. Sci. Symp. Med. Im. Conf., 2004, pp. 3151-3155.

M.W. Jacobson and J.A. Fessler, "Joint Estimation of Image and Deformation Parameters in Tomographic Image Reconstruction", In IEEE Workshop on Statistical Signal Processing, 2003, pp. 162-165 (4 pgs).

M.W. Jacobson and J.A. Fessler, "Joint Estimation of Image and Deformation Parameters in Motion-Corrected PET", In Proc. IEEE Nuc. Sci. Symp. Med. Im. Conf., vol. 5, 2003, pp. 3290-3294 (5 pgs).

R. Zeng, J.A. Fessler, and J.M. Balter, "Respiratory motion estimation from slowly rotating x-ray projections: Theory and simulation", Med. Phys., vol. 32, No. 4, Apr. 2005, pp. 984-991 (8 pgs).

R. Zeng, J.A. Fessler, and J.M. Balter, "Estimating 3D Respiratory Motion from Orbiting Views", 2003 IEEE Nuclear Science Symposium Conference, pp. 2399-2403 (5 pgs).

R. Zeng, J.A. Fessler, and J.M. Balter, "Estimating 3-D Respiratory Motion From Orbiting Views by Tomographic Image Registration", IEEE Transactions on Medical Imaging, vol. 26, No. 2, Feb. 2007, pp. 153-163 (11 pgs).

An extended EP search report, dated Nov. 15, 2011, for copending EP patent application No. EP08745876 (8 pgs).

S. Bonnet et al., "Dynamic X-Ray Computed Tomography," Proceedings of the IEEE, vol. 91, No. 10, Oct. 1, 2003, pp. 1574-1587.

J. Montagnat et al., "4D deformable models with temporal constraints: application to 4D cardiac image segmentation," Medical Image Analysis, Oxford University Press, vol. 9, No. 1, Feb. 1, 2005, pp. 87-100.

J. Montagnat et al., "Space and Time Shape Constrained Deformable Surfaces for 4D Medical Image Segmentation," Medical Image Computing and Computer-Assisted Intervention MICCAI International Conference Proceedings, Feb. 11, 2004, pp. 196-205.

M. Wernick et al., "Fast Spatio-Temporal Image Reconstruction for Dynamic PET," IEEE Transactions on Medical Imaging, vol. 18, No. 3, Mar. 1, 1999, pp. 185-195.

* cited by examiner

METHODS AND SYSTEMS FOR IMPROVING SPATIAL AND TEMPORAL RESOLUTION OF COMPUTED IMAGES OF MOVING OBJECTS

BACKGROUND OF THE INVENTION

This invention relates generally to image reconstruction and more particularly, to improving both temporal resolution and spatial resolution of a reconstructed image.

CT cardiac imaging is one of the most recent technological advancements in CT imaging; however at least some known methods of CT cardiac imaging are limited due to motion of the heart during the CT scan. As such, it is essential to collect the CT data when the motion of the heart is minimal. Therefore, at least some known methods of CT cardiac imaging collect data within a narrow temporal window that corresponds with a specific phase of the heart cycle.

Specifically, in some known CT cardiac imaging methods, filtered-backprojection (FBP) image reconstruction is used to reconstruct projection data that spans a sufficiently wide angular range. The data is grouped or merged into L datasets of measured projections such that each frame $y_m$ of the corresponding dataset can be reconstructed. For example, if L=2, a first dataset $z_1$ would equal $\{y_1 \ldots y_{M/2}\}$ and a second dataset $z_2$ would equal $\{y_{M/2+1} \ldots y_M\}$, wherein M denotes the total number of projection views. Typically, datasets $z_1$ and $z_2$ would be defined based upon an EKG signal. Frame $f_1$ is then reconstructed from dataset $z_1$ and frame $f_2$ is reconstructed from dataset $z_2$. As such, an image of the heart can be reconstructed for each phase of the cardiac cycle. Further, iterative reconstruction methods can also be used to reconstruct $f_1$ from dataset $z_1$ and $f_2$ from dataset $z_2$. However, using conventional iterative reconstruction to such grouped datasets does not improve temporal resolution relative to FBP image reconstruction because the grouping that defines the datasets $\{z_1\}$ determines the temporal resolution. In particular, conventional iterative methods and FBP methods require complete or nearly complete sets of projection views and this often requires longer time intervals over which object motion may occur.

BRIEF SUMMARY OF THE INVENTION

In one aspect, a method of improving a resolution of an image using image reconstruction is provided. The method includes acquiring scan data of an object and forward projecting a current image estimate of the scan data to generate calculated projection data. The method also includes applying a data-fit term and a regularization term to the scan data and the calculated projection data and modifying at least one of the data fit term and the regularization term to accommodate spatio-temporal information to form a reconstructed image from the scan data and the calculated projection data.

In another aspect, a system for reconstructing an image is provided. The system includes a processor configured to acquire scan data of an object and forward project a current image estimate of the scan data to generate calculated projection data. The processor is also configured to apply a data-fit term and a regularization term to the scan data and the calculated projection data and modify at least one of the data fit term and the regularization term to accommodate spatio-temporal information to form a reconstructed image from the scan data and the calculated projection data.

In a further aspect, a system for reconstructing a cardiac image is provided. The system includes a processor configured to acquire scan data of a heart and forward project a current image estimate of the scan data to generate calculated projection data. The processor is also configured to apply a data-fit term and a regularization term to the scan data and the calculated projection data and modify at least one of the data fit term and the regularization term to accommodate spatio-temporal information to form a reconstructed image from the scan data and the calculated projection data.

DETAILED DESCRIPTION OF THE INVENTION

Figure 1:
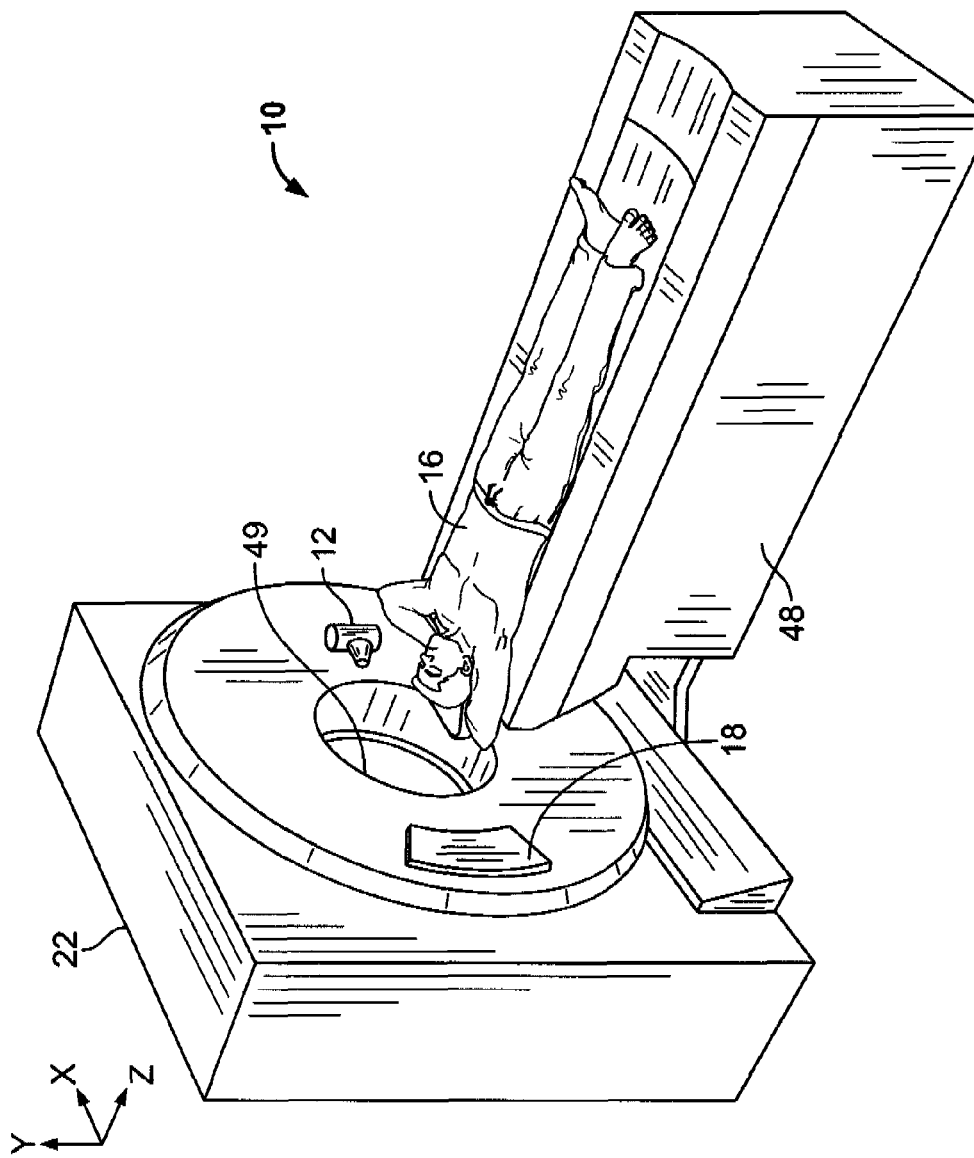
FIG. 1 is an isometric view of an embodiment of a computed tomography (CT) imaging system.
Figure 2:
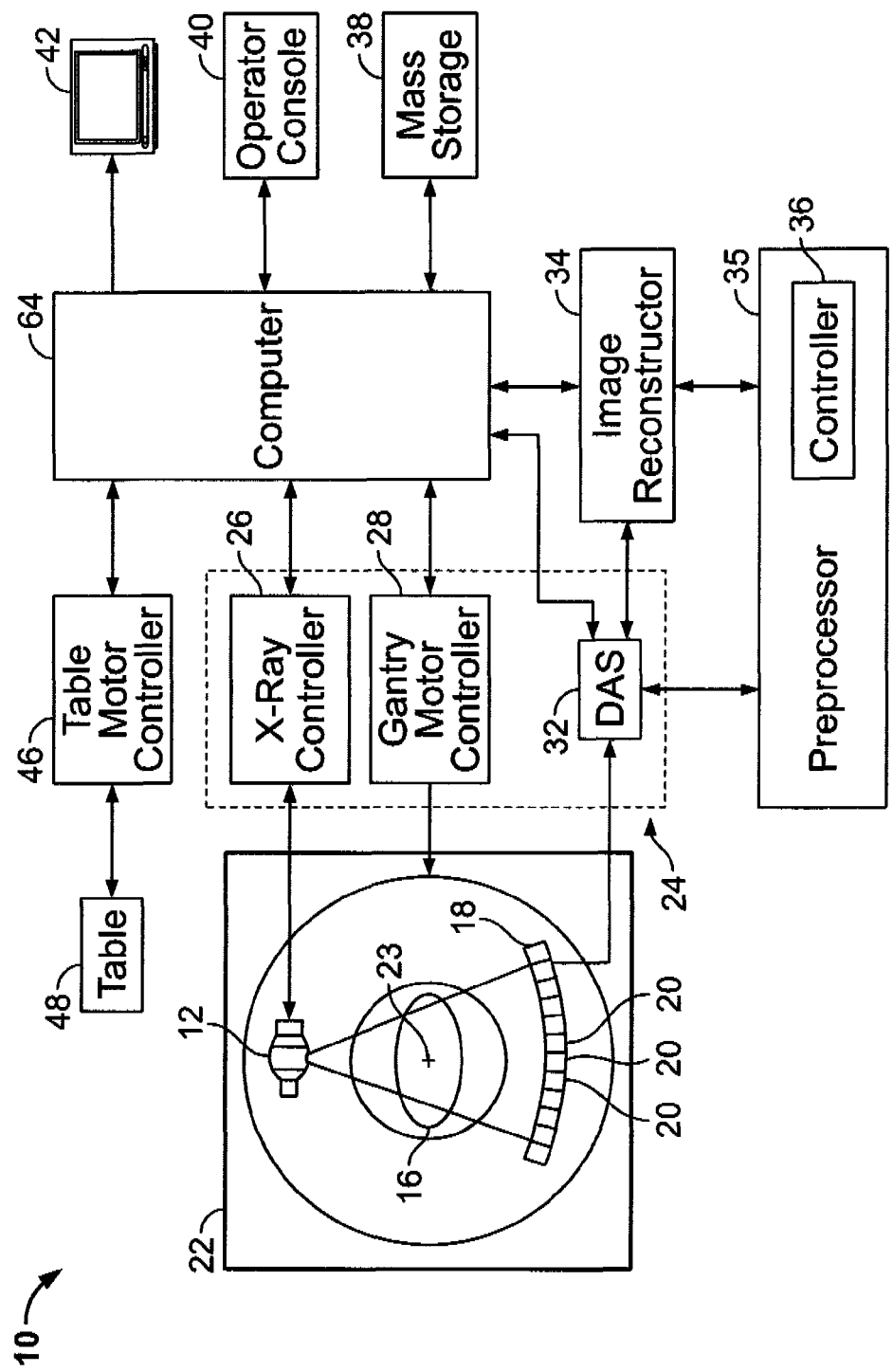
FIG. 2 is a block diagram of the CT system of FIG. 1.

FIGS. 1 and 2 illustrate an embodiment of a computed tomography (CT) imaging system 10. Specifically, FIG. 1 is an isometric view of an embodiment of computed tomography (CT) imaging system 10, and FIG. 2 is a block diagram of computed tomography (CT) imaging system 10. Although the present invention is described in terms of a CT imaging system, as will be appreciated by one skilled in the art, the methods described herein may also apply to X-ray computed tomography, magnetic resonance imaging, single photon emission computed tomography, positron emission tomography, or any other imaging system capable of utilizing the methods described herein.

CT imaging system 10 includes a gantry 22 and is a "third generation" CT system. In an alternative embodiment, CT system 10 may be an energy integrating, a photon counting (PC), or a photon energy discriminating (ED) CT detector system. Gantry 22 has an x-ray source 12 that projects a beam of x-rays toward a detector array 18. The x-rays pass through a subject 16, such as a patient, to generate attenuated x-rays. Subject 16 lies along a z-axis. A height of subject 16 is parallel to the z-axis. Detector array 18 is formed by a plurality of detector elements 20 which together sense the attenuated x-rays. A row of detector arrays 18 is located along an x-axis and a column of detector arrays 18 is located along a y-axis. In an alternative embodiment, each detector element 20 of detector array 18 may be a photon energy integrating detector, a photon counting, or a photon energy discriminating detector. Each detector element 20 produces an electrical signal that represents an intensity of the attenuated x-rays. During a scan to acquire projection data, gantry 22 and components mounted on gantry 22 rotate about a center of rotation 23.

Rotation of gantry 22 and an operation of x-ray source 12 are governed by a control mechanism 24 of CT system 10. Control mechanism 24 includes an x-ray controller 26 that provides power and timing signals to x-ray source 12 and a gantry motor controller 28 that controls a rotational speed and position of gantry 22. A data acquisition system (DAS) 32 in control mechanism 24 samples and digitizes the projection data from detector elements 20 and converts the projection data to sampled and digitized projection data for subsequent processing.

A pre-processor 35 including a controller 36 receives sampled and digitized projection data from DAS 32 to pre-process the sampled and digitized projection data. In one embodiment, pre-processing includes, but is not limited to, an offset correction, a primary speed correction, a reference channel correction, and an air-calibration. As used herein, the term controller is not limited to just those integrated circuits referred to in the art as a controller, but broadly refers to a processor, a microprocessor, a microcontroller, a programmable logic controller, an application specific integrated circuit, and other programmable circuits, and these terms are used interchangeably herein. Pre-processor 35 pre-processes the sampled and digitized projection data to generate pre-processed projection data.

An image reconstructor 34 receives the pre-processed projection data from pre-processor 35 and performs image reconstruction to generate a CT image. The CT image is applied as an input to a computer 64 which stores the CT image in a mass storage device 38. As used herein, each of the terms "computer" and "image reconstructor" is not limited to just those integrated circuits referred to in the art as a computer, but broadly refers to a processor, a microcontroller, a controller, a programmable logic controller, an application specific integrated circuit, and other programmable circuits, and these terms are used interchangeably herein. X-ray controller 26 adjusts a tube current within x-ray source 12 based on a quality of the CT image.

Computer 64 also receives commands and scanning parameters from a user, such as an operator, via a console 40 that has a user interface device. A display 42, such as a monitor, allows a user, such as an operator, to observe the CT image and other data from computer 64. Computer 64 uses the commands and scanning parameters to provide control signals and information to DAS 32, x-ray controller 26, and gantry motor controller 28. In addition, computer 64 operates a table motor controller 46 which controls a motorized table 48 to position and translate subject 16 within gantry 22. Particularly, table motor controller 46 adjusts table 48 to move portions of subject 16 and center subject 16 in a gantry opening 49.

In an alternative embodiment, a high frequency electromagnetic energy projection source configured to project high frequency electromagnetic energy toward subject 16 may be used instead of x-ray source 12. A detector array disposed within a gantry and configured to detect the high frequency electromagnetic energy may also be used instead of detector array 18.

Also as used herein, reconstruction of an image is not intended to exclude embodiments of the systems and methods for filtering a measurement of a density of an object in which data representing an image is generated but a viewable image is not. Many embodiments of the systems and methods for filtering a measurement of a density of an object generate or are configured to generate at least one viewable image.

Figure 3:
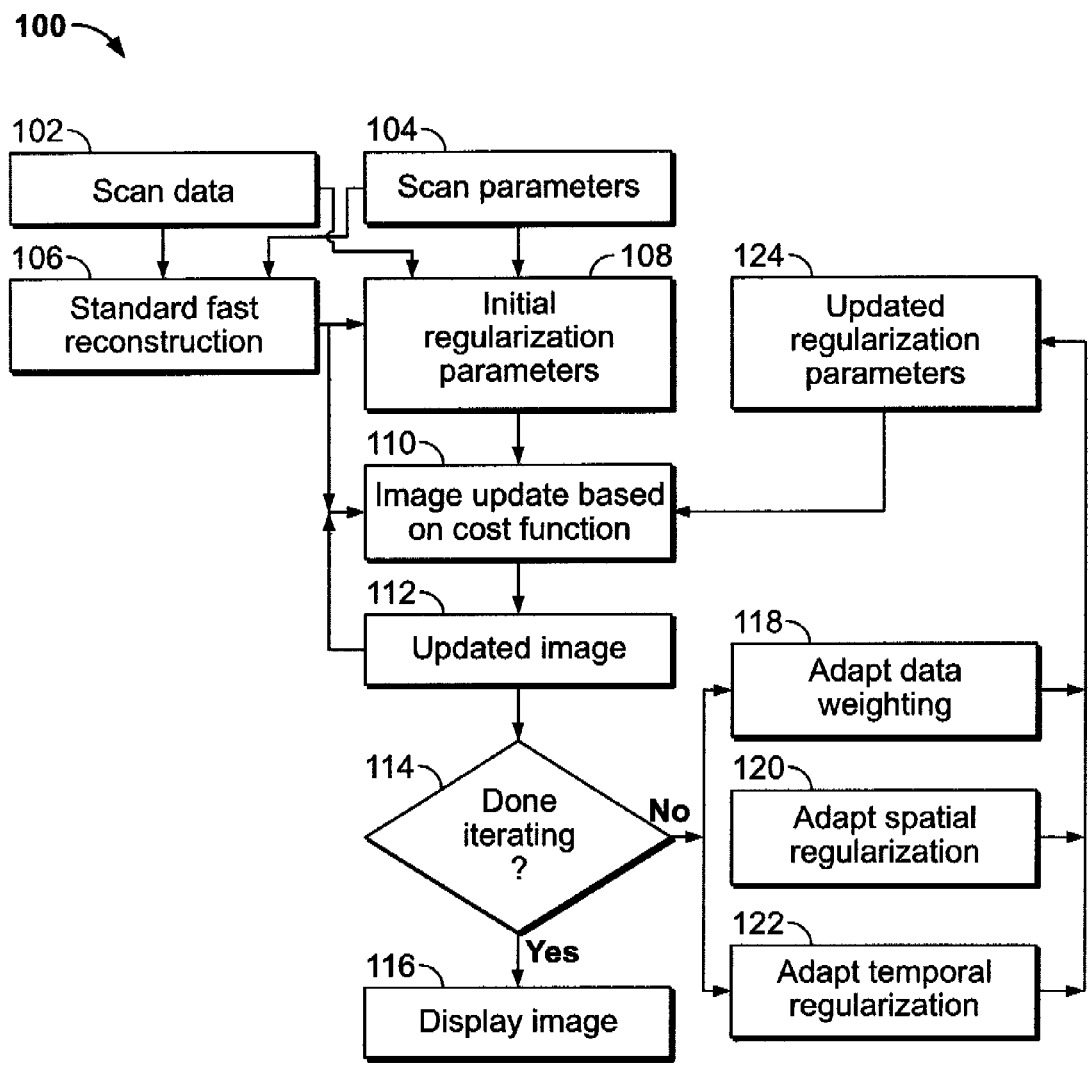
FIG. 3 is a flowchart of an embodiment of a method for improving a resolution of an image.

FIG. 3 is a flowchart 100 of an embodiment of a method for improving the resolution of an image. Specifically, FIG. 3 is a flowchart 100 of a method for improving temporal resolution and spatial resolution of a cardiac CT image by minimizing a cost function during iterative reconstruction by applying a data-fit term, a temporal regularization term, and a spatial regularization term to data acquired during a cardiac CT scan. While the present invention is described in terms of cardiac CT imaging, as will be appreciated by one skilled in the art, the methods described may also apply to CT imaging of any other object. Moreover, as will also be appreciated by one skilled in the art, the present invention may also apply to X-ray computed tomography, magnetic resonance imaging, single photon emission computed tomography, positron emission tomography, or any other imaging system capable of utilizing the methods described herein.

Referring back to FIGS. 2 and 3, computer 64 acquires scan data 102. In the exemplary embodiment the scan data includes M number of CT projection views. In alternative embodiments, the scan data includes at least one of M number of SPECT projection views, M portions of k-space data in MRI, or M number of coincidence events in PET. Moreover, acquiring scan data 102 may include acquiring scan data using at least one of continuous 1800 plus cardiac fan angle and less than 180° plus cardiac fan. Further, cone-beam scan data may be acquired. As such, the methods described herein may apply to single-sector or segmented image reconstruction, where data from a single heartbeat is used to reconstruct the image. Moreover, the same methods can also be applied to multi-sector reconstruction, where data from multiple heartbeats provide complementary angular ranges to reconstruct an image at a specific phase of the heart with higher temporal resolution.

The acquired image data includes $y_1$ through $y_M$ projection views that are recorded by the system. In the exemplary embodiment, a predetermined set of scan parameters 104 are programmed into computer 64 to dictate the parameters of the acquired image data that will be reconstructed. For example, for a 64-slice scanner with 1000 detector channels per slice and 980 projection views per rotation, each $y_m$ is a vector of length 64,000 elements, and a typical value for M, in one embodiment, would be a multiple of 980. Specifically, M would be equal to 980 projection views per rotation times the number of rotations. The object (i.e., the chest and heart of the patient) changes continuously throughout the scan, but in practice reconstruction is achieved using several "snapshots" or "frames" of pictures of the chest and heart over phases of a cardiac cycle. The "snapshots" or "frames" are grouped by letting $f_1$ through $f_L$ denote L image frames that are to be reconstructed from the measured projection data. In an exemplary embodiment, each frame would be a 512×512×200 volume and L would be between 2 and 16 frames. Therefore, each $f_l$ will be a vector of about 512*512*200 elements long.

Scan parameters 104 are used with scan data 102 during a standard fast reconstruction 106 (such as FBP). An output of standard fast reconstruction 106, scan data 102, and scan parameters 104 are then used to compute initial regularization parameters 108 to regularize the image data. Specifically, the initial regularization parameters include spatio-temporal data-weighting factors, $w_{ml}$, temporal regularization parameters, $t_{lj}$, and spatial regularization parameters, $s_{jk}$. Initial regularization parameters 108 are predetermined prior to the beginning of image reconstruction and used to reconstruct the image by minimizing a cost function 110 that consists of three terms: a data-fit term, a temporal regularization term, and a spatial regularization term. Mathematically the minimization can be expressed as follows:

$$f = \mathrm{argmin}_f D(f) + T(f) + S(f), \qquad (1)$$

where $f = (f_1, \ldots, f_L)$ and D(f) represents the data-fit term, T(f) represents the temporal regularization term, and S(f) represents the spatial regularization term, respectively.

In the exemplary embodiment, the data-fit term is weighted as follows:

$$D(f) = \sum_{m=1}^{M} \sum_{l=1}^{L} w_{ml} d(y_m, A_m f_l), \qquad (2)$$

where $A_m$ denotes a system model or forward projection operator and $d(y_m, A_m f_l)$ denotes a measure of distance between the measured projection data $y_m$ and the predicted or reprojected data $A_m f_l$. In one embodiment, $d(y_m, A_m f_l)$ will include weighting based on known statistics of the data. For example, known statistics of the data may include at least one of a Poisson, Gaussian, or compound-Poisson distribution, or combinations thereof.

Further, in the exemplary embodiment, the temporal regularization term is weighted as follows:

$$T(f) = \sum_{l=2}^{L} \sum_{j=1}^{J} t_{lj} p(f_{l,j} - f_{l-1,j}), \qquad (3)$$

where p(.) denotes a first "potential function", such as, but not limited to the Huber function or a quadratic function, as are known in the art, and J denotes a number of voxels in each image. In the exemplary embodiment, the temporal regularization parameters, $t_{ij}$, are selected to improve temporal resolution.

Moreover, in the exemplary embodiment, the spatial regularization term is weighted as follows:

$$S(f)=\sum_{j=1}^{J}\sum_{k=1}^{K}s_{jk}p(f_{l,j}-f_{l,j-n_k}), \quad (4)$$

where K denotes a number of spatial neighbors of each image, $n_k$ denotes a relative index of the kth neighbor, and p(.) denotes a second "potential function", such as, but not limited to the Huber function or a quadratic function, as are known in the art. In the exemplary embodiment, the spatial regularization parameters, $s_{jk}$, are selected to improve spatial resolution.

By minimizing the cost function 110, an updated image 112 is produced. Computer 64 then determines 114 if all iterations of the reconstruction have been completed. If the iterations have been completed, a reconstructed image is displayed 116 on display 42. If the iterations are not completed, the initial regularization parameters are adjusted by computer 64 and reapplied to cost function 110 to update image 112.

Specifically, in the exemplary embodiment, the spatio-temporal data-weighting factor is adjusted 118 based on where a projection data m falls in the cardiac cycle relative to the cardiac phase l, resulting in phase-weighted iterative reconstruction. In the exemplary embodiment, $w_{ml}$ is selected adaptively to improve temporal resolution. Specifically $w_{ml}$ is adjusted based on how well a predicted data from the current image estimate matches the projection view $y_m$. In an alternative embodiment, other considerations are used to selectively adapt $w_{ml}$, such as, but not limited to whether the data corresponds to a dynamic portion of the scanned object. In addition, $A_m$ is adjusted dynamically based on the state of the heart motion. Specifically, for a forward projection, the matrix can be "warped" dynamically based on any a prior knowledge of the heart motion. Such prior knowledge may include, but is not limited to motion vectors determined from earlier recons or from other sensors or imagers. Moreover, after a number of iterations, an intermediate estimate of the heart motion can be used to adapt the system model $A_m$, followed by more (improved) iterations.

Further, in the exemplary embodiment, the spatial regularization parameters $s_{jk}$ are adjusted 120 adaptively, based on how the voxel values change over time. For example, for voxels indexed by values of j corresponding to image regions that are far from the heart wall, less motion is expected; and therefore, larger values for the regularization parameters in those regions are utilized. Moreover, for voxels indexed by values of j corresponding to image regions that are close to the heart wall, more motion is expected; and therefore, smaller values for the regularization parameters in those regions are utilized to maximize the spatial resolution in those regions. For example, one could set $s_{jk}=\exp(-ad_j)$ where $d_j$ denotes the distance of the jth voxel from the heart wall and a is a tuning parameter that is selected empirically. Furthermore, for image frames l corresponding to the resting portions of the cardiac cycle (end diastole or end systole), larger values of the regularization parameters are used, compared to time frames where the heart is moving rapidly.

Moreover, in the exemplary embodiment, the temporal regularization parameters 122 are adjusted adaptively, based on considerations such as the spatial location and temporal characteristics of the voxel. More specifically, for voxel indices j within the heart region, smaller values of the temporal regularization parameters are utilized to maximize image quality in those regions. Further, in regions away from the heart, larger values of the temporal regularization parameters are utilized to reduce noise in the reconstructed image.

In an alternative embodiment, other considerations are used to selectively adapt the temporal regularization parameters 122, such as, but not limited to, using an ECG signal (or a so-called pseudo-ECG signal) to guide the design of the regularization parameters. As such, the shape of the ECG vector is analyzed and the state of the cardiac motion is determined or estimated to take full advantage of the patient's cardiac motion characteristics variation reflected in the ECG signal. Specifically, the regularization parameters are adapted both spatially and temporally.

The adjusted parameters 124 are reapplied to cost function 110 to further update image 112. The process of adjusting the regularization parameters 118, 120, 122 is repeated until all iterations of the image are completed and a final image 116 is displayed.

In the spatial and temporal regularization terms above, as is known in the art, higher-order differences may be utilized instead of the first-order differences that are shown above.

In iterative reconstruction, multiple iterations are needed to optimize the cost function. In the absence of a motion map, intermediate results in the optimization process may be utilized to further adjust or estimate the motion parameters. For example, at the end of every iteration, a difference between images reconstructed at different phases of the heart cycle may provide spatial and temporal information as to the direction of motion. As such, the regularization parameters may be adjusted to smooth less along the direction of motion and more along the orthogonal direction.

In one embodiment, a method of improving a resolution of an image using image reconstruction is provided. The method includes acquiring scan data of an object and forward projecting a current image estimate of the scan data to generate calculated projection data. The method also includes applying a data-fit term and a regularization term to the scan data and the calculated projection data and modifying at least one of the data fit term and the regularization term to accommodate spatio-temporal information to form a reconstructed image from the scan data and the calculated projection data. In one embodiment, the method also includes applying the equation $f^*=\mathrm{argmin}_f D(f)+T(f)+S(f)$ to the scan data, wherein $f=(f_1, \ldots, f_L)$ and represents L number of image frames that are being reconstructed, D(f) is the data-fit term, T(f) is a temporal regularization term, and S(f) is a spatial regularization term.

In the exemplary embodiment, the step of applying a data-fit term includes applying a data-fit term that includes a forward projection operator and temporal data-weighting factors, dynamically adjusting the forward projection operator based on a state of the object's motion, and adaptively selecting the temporal data-weighting factors based on a relationship between a predicted image and a projected view of the image.

Further, in one embodiment, the step of applying at least one regularization term includes adaptively selecting temporal regularization parameters based on an amount of object motion within an individual voxel of the image data. The at least one regularization term is modified by selecting a larger parameter for substantially motionless voxels and selecting a smaller parameter for voxels having substantial motion.

Moreover, in another embodiment, the step of applying at least one regularization term includes adaptively selecting a spatial regularization parameter based on a distance from an individual voxel to the object. The at least one regularization term is modified by selecting a larger parameter for voxels substantially within the object and selecting a smaller parameter for voxels substantially outside of the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

The above-described method for reconstructing an image facilitates providing a reconstructed image of a moving object having both improved spatial resolution and temporal resolution. The method includes regularizing both spatial and temporal parameters after every iteration. As a result, the above-described method facilitates providing an improved image quality, as compared to prior art methods.

Although the methods and systems described herein are described in the context of cardiac CT image reconstruction, it is understood that the methods and systems described herein are not limited computed tomography. Likewise, the methods described are not limited to cardiac imaging, but rather, can be utilized to reconstruct an image of any object, whether moving or stationary.

While the invention has been described in terms of various specific embodiments, those skilled in the art will recognize that the invention can be practiced with modification within the spirit and scope of the claims.

What is claimed is:

1. A method of improving a resolution of an image using image reconstruction, said method comprising:
   acquiring scan data of an object;
   forward projecting a current image estimate of the scan data to generate calculated projection data;
   applying a data-fit term and a regularization term to the scan data and the calculated projection data to form a reconstructed image of the object;
   iteratively modifying regularization term based on spatio-temporal information and change in voxel value over time; and
   applying said modified regularization term to the scan data and calculated projection data to form an updated reconstructed image of the object.

2. The method of claim 1 further comprising applying the equation $f^*=\mathrm{argmin}_f D(f)+T(f)+S(f)$ to the scan data, wherein $f=(f_1, \ldots, f_L)$ and represents L number of image frames that are being reconstructed, $D(f)$ is the data-fit term, $T(f)$ is a temporal regularization term, and $S(f)$ is a spatial regularization term.

3. The method of claim 1, wherein applying a data-fit term further comprises:
   applying a data-fit term that includes a forward projection operator and temporal data-weighting factors;
   dynamically adjusting the forward projection operator based on a state of the object's motion; and
   adaptively selecting the temporal data-weighting factors based on a relationship between a predicted image and a projected view of the image.

4. The method of claim 1, wherein applying a regularization term further comprises adaptively selecting temporal regularization parameters based on an amount of object motion within an individual voxel of the image data.

5. The method of claim 4, wherein modifying the regularization term further comprises:
   selecting a larger parameter for substantially motionless voxels; and
   selecting a smaller parameter for voxels having substantial motion.

6. The method of claim 1 wherein applying a regularization term further comprises adaptively selecting a spatial regularization parameter based on a distance from an individual voxel to the object.

7. The method of claim 6, wherein modifying the regularization term further comprises:
   selecting a larger parameter for voxels substantially within the object; and
   selecting a smaller parameter for voxels substantially outside of the object.

8. A system for reconstructing an image, said system comprising a processor configured to:
   acquire scan data of an object;
   forward project a current image estimate of the scan data to generate calculated projection data;
   apply a data-fit term and a regularization term to the scan data and the calculated projection data to form a reconstructed image of an object;
   iteratively modify the regularization term based on spatio-temporal information and change in voxel value over time; and
   applying said modified regularization term to the scan data and calculated projection data to form an updated reconstructed image of the object.

9. The system of claim 8, wherein said processor is further configured to apply the equation $f^*=\mathrm{argmin}_f D(f)+T(f)+S(f)$ to the scan data, wherein $f=(f_1, \ldots, f_L)$ and represents L number of image frames that are being reconstructed, $D(f)$ is the data-fit term, $T(f)$ is a temporal regularization term, and $S(f)$ is a spatial regularization term.

10. The system of claim 8, wherein said processor is further configured to:
    apply a data-fit term that includes a forward projection operator and temporal data-weighting factors;
    dynamically adjust the forward projection operator based on a state of the object's motion; and
    adaptively select the temporal data-weighting factors based on a relationship between a predicted image and a projected view of the image.

11. The system of claim 8, wherein said processor is further configured to apply the regularization term by adaptively selecting temporal regularization parameters based on an amount of object motion within an individual voxel of the image data.

12. The system of claim 11, wherein said processor is further configured to:
    select a larger parameter for substantially motionless voxels; and
    select a smaller parameter for voxels having substantial motion.

13. The system of claim 8, wherein said processor is further configured to apply the regularization term by adaptively selecting a spatial regularization parameter based on a distance from an individual voxel to the object.

14. The system of claim 13, wherein said processor is configured to:
    select a larger parameter for voxels substantially within the object; and
    select a smaller parameter for voxels substantially outside of the object.

15. A system for reconstructing a cardiac image, said system comprising a processor configured to:
    acquire scan data of a heart while a subject including the heart and a scanning device are moving relative to one another in at least two planes;
    forward project a current image estimate of the scan data to generate calculated projection data;

apply a data-fit term and a regularization term to the scan data and the calculated projection data; and modify regularization term to accommodate spatio-temporal information and change in voxel value over time to form a reconstructed image from the scan data and the calculated projection data.

16. The system of claim 15, wherein the processor is further configured to apply the equation $f=\mathrm{argmin}_f D(f)+T(f)+S(f)$ to the scan data, wherein $f=(f_1, \ldots, f_L)$ and represents L number of image frames that are being reconstructed, D(f) is the data-fit term, T(f) is a temporal regularization term, and S(f) is a spatial regularization term.

17. The system of claim 15, wherein said processor is further configured to apply the data-fit term to the scan data by applying the equation $D(f)=\Sigma_{m=1}^{M}\Sigma_{l=1}^{L}w_{ml}d(y_m, A_m f_l)$, where m is one of $y_1$ to $y_m$ measured projection views, wml is a temporal data weighting factor, $A_m$ is model or forward projection operator, $A_m f_l$ is reprojected data, and $d(y_m, A_m f_l)$ is a measure of distance between $y_m$ and $A_m f_l$.

18. The system of claim 17, wherein said processor is further configured to dynamically adjust $A_m$ based on a state of heart motion.

19. The system of claim 15, wherein said processor is further configured to apply the regularization term to the image data by applying the equation $T(f)=\Sigma_{l=2}^{L}\Sigma_{j=1}^{J}t_{lj}p(f_{lj}-f_{l-1,j})$, where j is a number of voxels in each image, p(.) is the potential function, and $t_{lj}$ is a temporal regularization parameter.

20. The system of claim 15, wherein said processor is further configured to apply the regularization term by applying the equation $S(f)=\Sigma_{j=1}^{J}\Sigma k=1^{K}s_{jk}p(f_{lj}-f_{l,j-n_k})$, where K is a number of spatial neighbors of each image, $n_k$ is a relative index of the kth neighbor, and p(.) is a potential function.

* * * * *